United States Patent [19]

Christophe et al.

[11] Patent Number: 5,674,890
[45] Date of Patent: Oct. 7, 1997

[54] COMPOUNDS BEARING SULPHAMOYL AND AMIDINO RADICALS, THEIR PREPARATION PROCESS AND PHARMACEUTICAL COMPOSITIONS CONTAINING THEM

[75] Inventors: Bernard Christophe, Grand Rosière, Belgium; Loïc Foulon, Pinsaguel, France; Alain Pellet, Beaumont sur Leze, France; Claudine Serradeil-Le Gal, Escalquens, France; Gérard Valette, Lacroix Falgarde, France

[73] Assignee: Sanofi, Paris, France

[21] Appl. No.: 582,887

[22] Filed: Jan. 4, 1996

Related U.S. Application Data

[62] Division of Ser. No. 195,281, Feb. 14, 1994, Pat. No. 5,506,258.

[30] Foreign Application Priority Data

Feb. 15, 1993 [FR] France ..................... 93 01686

[51] Int. Cl.$^6$ .......... C07D 333/22; C07D 409/12; C07D 413/12; A61K 31/38
[52] U.S. Cl. .............. 514/438; 549/65; 549/59; 549/60; 549/77; 548/527; 548/540; 548/311.1; 548/311.7; 548/315.1; 548/465; 546/213; 546/281.4; 546/280.4; 544/146; 544/379; 544/333; 514/422; 514/256; 514/385; 514/252; 514/336; 514/397; 514/444; 514/445
[58] Field of Search ................ 548/540, 311.1, 548/311.7, 315.1, 527, 465; 544/333, 146, 379; 514/422, 252, 256, 336, 385, 397, 444, 445, 438, 317, 231.5, 269, 414; 549/65, 77, 59, 60; 546/213, 281.4, 280.4

[56] References Cited

U.S. PATENT DOCUMENTS 4,791,102 12/1988 Bernat et al. .................. 514/19
5,348,976 9/1994 Shibata et al. ................. 514/469

FOREIGN PATENT DOCUMENTS 0236163 9/1987 European Pat. Off. .
9108223 6/1991 WIPO .

OTHER PUBLICATIONS

M.C. Michel et al., "Neuropeptide Y and its antigonists", Drugs of the Future vol. 17, No. 1, 1992, pp. 39–45.

*Primary Examiner*—Johann Richter
*Assistant Examiner*—Laura R. Cross
*Attorney, Agent, or Firm*—Jacobson, Price, Holman & Stern, PLLC

[57] ABSTRACT

A compound of formula I

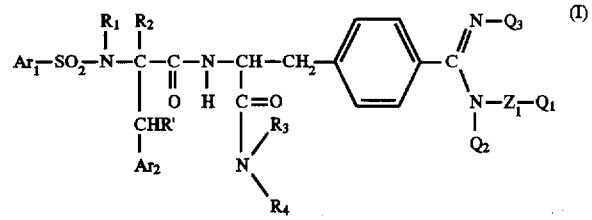

in which $Ar_1$ is naphthyl and phenyl, quinolyl or isoquinolyl optionally substituted; $Ar_2$ is phenyl or thienyl optionally substituted; $R_1$, $R_2$ and $R'_2$ are independently of each other H or $(C_1-C_4)$alkyl or $R_1$ represents a bond and N is covalently bonded to $Ar_2$, and optionally $R_2$ and $R'_2$ form a double bond, or $R_1$ or $R_2$ is covalently bonded to $Ar_2$ and represents a $(C_1-C_3)$alkylene; $R_3$ and $R_4$ are independently of each other H or $(C_1-C_4)$alkyl or form, with the nitrogen atom to which they are attached pyrrolidine, ppiperidine, or hexahydroazepine; $Z_1$ represents $(C_1-C_{12})$alkylene, optionally interrupted by a radical selected from the group consisting of $(C_5-C_7)$cycloalkyl and phenyl or substituted with a radical selected from the group consisting of $(C_5-C_7)$ cycloalkyl and phenyl; $Q_1$ is selected from the group consisting of methyl, amino, $(C_1-C_4)$alkoxycarbonylamino, $(C_1-C_4)$alkylamino, di$(C_1-C_4)$-alkylamino, pyrrolidinyl, piperidino, morpholino, piperazinyl, 4-$(C_1-C_4)$ alkylpiperazinyl, amidino, $(C_1-C_4)$-alkylamidino, guanidino, $(C_1-C_4)$alkylguanidino, pyridyl, imidazolyl, pyrimidinyl, indolyl, hydroxy,$(C_1-C_4)$alkoxy,$(C_2-C_8)$ alkoxycarbonyl,N-[amino$(C_1-C_4)$alkyl]-N-[$(C_1-C_4)$alkyl] amino, carbamoyl, phenyl and phenyl substituted by a radical selected from the group consisting of Cl, F, $(C_1-C_4)$ alkyl, $(C_1-C_4)$alkoxy and hydroxyle; $Q_2$ is selected from the group consisting of H and $(C_1-C_4)$alkyl; $Q_3$ is selected from the group consisting of H and $(C_1-C_4)$alkyl or $Q_1$ and $Q_3$ are attached to form a heterocycle and together represent $(C_2-C_3)$alkylene, whereas $Z_1$ represents a bond, in the form of pure enantiomer or mixture thereof in any proportions as well as its salt with acid.

7 Claims, No Drawings

COMPOUNDS BEARING SULPHAMOYL AND AMIDINO RADICALS, THEIR PREPARATION PROCESS AND PHARMACEUTICAL COMPOSITIONS CONTAINING THEM

This is a divisional of U.S. application Ser. No. 08/195,281 filed Feb. 14, 1994 now U.S. Pat. No. 5,506,258.

The present invention relates to new compounds containing, simultaneously, especially a substituted sulphamoyl and an amidino group, to the process for preparing them and to pharmaceutical compositions containing them.

These compounds have in particular a certain affinity for the biological receptors of neuropeptide Y, NPY, which are present in the central and peripheral nervous systems.

Neuropeptide Y was identified only about ten years ago, and very few agonists or antagonists are currently known for its receptors which are not polypeptides, whose use in therapy is not easy, especially because of their degradation in the gastrointestinal tract; a recent review in Drugs of the Future 17 (1) 39–45 (1992) mentions benextramine, an inositol phosphate and an antihistamine derived from guanidinoalkylimidazole.

Compounds with a structure similar to that of the compounds of the invention have been described in EP-A-0,236,163 and EP-A-0,236,164; they correspond to the formula A;

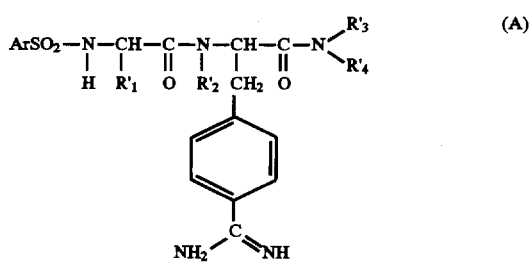

in which $R'_1$, $R'_2$, $R'_3$ and $R'_4$ are especially alkyls or phenyls. These compounds are anticoagulants and antithrombotic agents, such that this document could not suggest the activity of the present compounds.

The compounds of the invention correspond to the formula I:

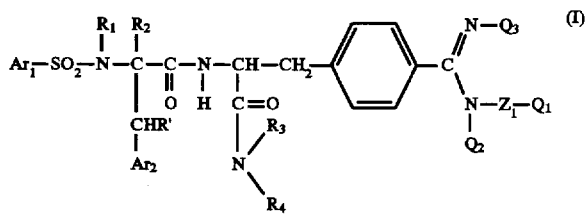

in which $Ar_1$ represents naphthyl, phenyl, quinolyl or isoquinolyl optionally substituted by Cl, F, $(C_1-C_4)$alkyl, $(C_1-C_4)$alkoxy hydroxy or $(C_1-C_4)$dialkylamino;

$Ar_2$ represents a phenyl or thienyl optionally substituted by Cl, F, $(C_1-C_4)$alkyl, $(C_1-C_4)$alkoxy or hydroxy;

$R_1$, $R_2$ and $R'_2$ are independently of each other, H or $(C_1-C_4)$alkyl; or $R_1$ represents a bond and N is covalently bonded to $Ar_2$, and optionally $R_2$ and $R'_2$ form a double bond;

or $R_1$ or $R_2$ is covalently bonded to $Ar_2$ and represents a $(C_1-C_3)$ alkylene;

$R_3$ and $R_4$, which are identical or different, represent H, $(C_1-C_4)$alkyl or form, with the nitrogen atom to which they are attached, a $(C_5-C_7)$ saturated heterocycle selected from pyrrolidine, piperidine and hexahydroazepine;

$Z_1$ represents a $(C_1-C_{12})$alkylene, optionally interrupted or substituted by a $(C_5-C_7)$cycloalkyl or phenyl;

$Q_1$ represents methyl, amino, alkoxycarbonylamino, alkylamino, dialkylamino, a $(C_5-C_7)$ saturated heterocyclic amino group, amidino, alkylamidino, guanidino, alkylguanidino, pyridyl, imidazolyl, pyrimidinyl, indolyl, hydroxy, alkoxy, $(C_2-C_8)$alkoxycarbonyl, amino$(C_1-C_4)$ alkyl-N-$(C_1-C_4)$alkylamino or carbamoyl, phenyl or phenyl substituted by Cl, F, $(C_1-C_4)$alkyl, $(C_1-C_4)$alkoxy or hydroxy;

$Q_2$ represents H or alkyl;

$Q_3$ represents H or $(C_1-C_4)$alkyl;

or $Q_1$ and $Q_3$ are attached to form a heterocycle and together represent a $(C_2)$ or $(C_3)$alkylene, whereas $Z_1$ represents a bond, and the addition salts of these compounds with acids.

The linear or branched alkyl and alkoxy groups correspond to $(C_1-C_4)$ unless otherwise indicated; the saturated heterocyclic amino groups may be pyrrolidinyl, piperidino, morpholino, piperazinyl or 4-alkylpiperazinyl. The phenyls, unless otherwise indicated, may be substituted by Cl, F, $(C_1-C_4)$alkyl, $(C_1-C_4)$alkoxy or hydroxy.

The salts are generally prepared with pharmaceutically acceptable acids but the salts of other acids which are useful for the purification or isolation of the products of formula I also form part of the invention.

The compounds of formula I comprise in general two asymmetric carbons and the 4 pure enantiomers as well as mixtures thereof, in any proportions, are within the invention.

The compounds according to the invention can be prepared from the compounds of formula II:

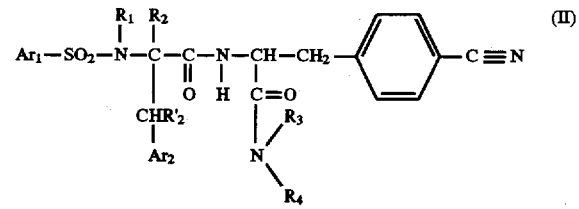

by processes whose principles are known, which a person skilled in the art will be able to adapt to the reactivity and solubility of the products used.

Many processes for the synthesis of amidines are described in the book "The chemistry of amidines and imidates" D. G. Neilson Ed Saul Patai; Wiley & Sons—p. 389–394 (1975). In general, the nitrile is converted to an imidate salt by reacting an alcohol in a strong acid medium, in a so-called Pinner reaction, and this imidoester, optionally in free form, is reacted with the amine of formula III:

in a non-reactive polar solvent, preferably in an alcohol, at a temperature of between 0° C. and the reflux temperature of the solvent.

Most of these amines (III) are known and the new products can be prepared by applying principles and methods well known to a person skilled in the art. For example, for the derivatives in which $Q_1$ is an imidazolyl, reference can be made to U.S. Pat. No. 3,881,016 and to Synth. Communic. 17, 223–227 (1987) or when $Q_1$ is a t-butoxycarbonylamino group, to Synth. Communic. 20 (16), 2559–2564 (1990).

The compounds of formula I in which $Q_1$ represents $NH_2$ or alkylamino can be prepared by hydrolysis of the compounds of formula I in which $Q_1$ is a t-butoxycarbonylamino group.

The compounds of formula I in which $Q_1$ represents a substituted or unsubstituted guanidino group can be prepared, by reacting with the compound in which $Q_1=NH_2$, a compound of formula

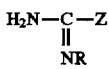

in which R represents H or alkyl and Z represents a nucleofuge, such as $SO_3H$, for example under the conditions described in Tetrahedron Letters 3183–3186 (1988) with aminoiminomethanesulphonic acid; the N-methylamino-iminomethanesulphonic acid can be obtained as described in J. Org. Chem. 51 1882 (1986).

The compounds of formula I in which the amidine group is included in a heterocycle can be prepared in a manner known per se by reacting a diamine $H_2N—(CH_2)_n—NH_2$ in which n is 2 or 3, with the imidoester, optionally by reacting a diamine in which one of the groups is protected by a labile group which will be removed before cyclization.

A certain number of processes for the preparation of the nitriles of formula II in which $Ar_1$ is naphthyl, $R_1=R_2=R'_2=H$ are described in EP-A-0,236,163 and reference can be made thereto, especially for preparing the pure enantiomers from each pure stereoisomer of 4-cyano-phenylalanine in which the carboxylic acid group will be blocked, optionally, in the form of an amide substituted by $R_3$ and $R_4$ as in formula I; this compound will be reacted with the alpha-amino acid of formula IV:

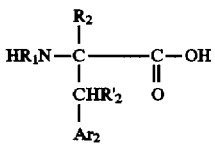 IV in which the amino group will be protected beforehand either in the form of sulphamoyl

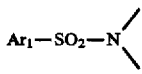

as in formula I, or by a labile group such as t-butoxycarbonyl, which will be removed after the coupling, in a conventional manner, by reaction of a strong anhydrous acid.

Processes for the preparation of amides by reaction of a carboxylic group and an amino group, which are carried by 2 asymmetric carbons, without racemization around any one of these carbons, can also be found in numerous publications relating to the chemistry of peptides and especially in: The Peptides. Ed. E. Cross and J. Meienhofer vol. 1, 65–104 (1979)—Acad. Press.

In general, these reactions occur at temperatures of between 0° and 40° C., in an inert solvent such as dichloromethane, acetonitrile, tetrohydrofuran or dimethylformamide, in the presence of at least one equivalent of a tertiary amine such as triethylamine or preferably in the presence of N-ethylmorpholine.

The sulphamoyl group

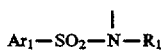

can be obtained in a conventional manner, by reacting a sulphochloride $Ar_1—SO_2—Cl$ in the presence of a base, optionally in a two-phase medium, in the presence of a phase transfer catalyst either with the amino acid IV or a corresponding alkyl ester, or with the nitrile of formula V:

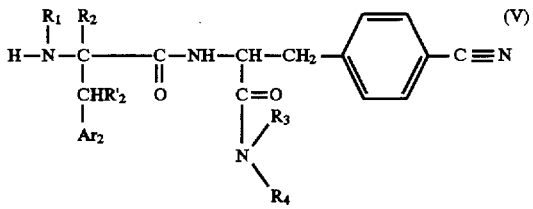

When $R_1$ is different from H, the nitriles II can be obtained by reacting $R_1X$ with the sulphonamide II in which $R_1$ is H, in the presence of a base, X representing a halogen atom or a sulphonate group.

The alpha-amino acids of formula IV or the corresponding aliphatic esters are known compounds or can be prepared by processes similar to those used for the known derivatives. Reference is especially made to Greenstein and M. Winitz in "Chemistry of the amino acids", J. Wiley and Sons Inc. ed., (1961) p. 697–714 and p. 2693–2770, and G. C. Barrett in "Chemistry and Biochemistry of the amino acids", Chapman and Hall ltd. ed., 1985, p. 246–353. For example, when $R'_2=H$, by means of a Schiff base as described in Synthesis 313–315 (1984), according to the reaction scheme:

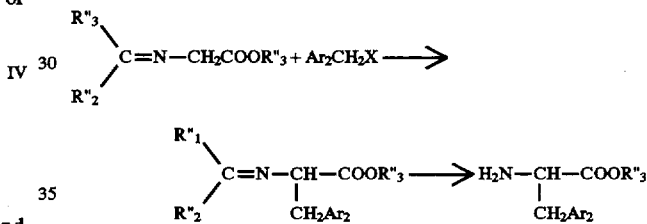

in which $R''_1$ and $R''_2$, represent phenyl rings, $R''_3$ represents alkyl and $Ar_2$ has the same meaning as in formula I.

The amino acids of formula IV in which $R_2$ is different from H may be obtained via a similar route. In this case, the Schiff base is successively alkylated by $Ar_2CH_2X$ and $R_2X$ in tetrahydrofuran in the presence of a base such as an alkali metal alkoxide at $-70°$ C.–+25° C.

In order to obtain the amino acids of formula IV, or the corresponding esters in the form of one of the pure enantiomers, fractional recrystallizations of a salt of the racemate can be carried out with an optically active acid or base, according to a technique whose principle is well known; one of the enantiomers of a racemic ester of an amino acid of formula IV can also be separated in the form of the corresponding amino acid by carrying out an enzymatic hydrolysis of the racemic mixture with a stereoselective enzyme such as alpha-chymotrypsin, a method which is described especially in Journal of Biochemistry 19, 877–881 (1971).

The salts of the compounds of formula I are prepared by reacting the chosen acids with the amidine of formula I, in a solvent; the salts obtained are isolated after distillation of the solvent or addition of a non-solvent in order to precipitate them.

The compounds of formula I and their pharmaceutically acceptable salts bind to the biological receptors of neuropeptide Y (NPY), a 36-amino acid peptide whose physiological activities are many, especially in the central nervous or cardiovascular system. NPY regulates psychomotor activity, anxiety and sedation, it is a stimulant of food intake; it plays a role in depression, memorization processes, certain sexual behaviours and epilepsy; it inhibits the secretion of insulin, glucagon and luteinizing hormone; it acts in the kidneys and especially on the renin-angiotensin system; finally, it is a potent vasoconstrictor. Reference can be made to a review published in Drugs of the Future 17 (1) 39–45 (1992) which also mentions potential therapeutic activities of the antagonists of NPY.

The affinity of the compounds of the invention for the NPY receptors can be demonstrated in vitro using the method described by Unden et al., in Eur. J. Biochem 145 525–530 (1984) on rat cortex membranes; under these conditions, the compounds of the invention which are exemplified hereinafter have $IC_{50}$ values (concentration inhibiting 50% of the binding of NPY to its receptor) of between 10 nM and 10 µM, whereas that for NPY is 0.5 nM.

Compounds displaying affinity for the NPY receptors may be agonists or antagonists of the action of the peptide NPY on its receptor.

The antagonistic activity of NPY can be demonstrated by applying the method described in Proc. Soc. Exp. Biol. Med. 64 453–455 (1947) in pithed rats; under these conditions, the administration of NPY has a hypertensive effect which is reduced or even suppressed when the animals are treated with an antagonist of the invention.

For the compounds having a strong affinity for the receptors, $ID_{50}$ values of a few µg/kg have been measured during i.v. perfusions of 10 µg/kg of NPY.

Currently, no specific antagonist, of high affinity and competitive, is known and the compounds according to the invention are particularly valuable; they can be advantageously used as antihypertensive agents or for the treatment of angina pectoris especially for their vasodilating activity, or for combating coronary and cerebral vasospasms, as well as in the treatment of atherosclerosis and congestive heart failure. These compounds can also be used as anorectic agents, antidepressants or tranquilizers, for reducing anxiety or regulating certain sexual behaviour disorders. They will also be of real interest in the treatment of inflammation, allergy, certain gastrointestinal disorders, such as Crohn's disease or the regulation of the food intake or alternatively in that of excess fats, given lipolytic activity; they are also immune modulators. They may be used in all the pathologies or disorders NPY dependent.

Thus, the invention also relates to the pharmaceutical compositions comprising as active ingredient one of the enantiomers of the compounds of formula I, one mixture thereof or their salts with a pharmaceutically acceptable acid, as well as an excipient suitable for administration by the oral route, by injection or by the transdermal route. The daily doses will depend on the pathology to be treated and on the patient.

The invention relates to pharmaceutical compositions containing a therapeutically effective amount of a compound according to the invention or any pharmaceutically acceptable salt thereof and suitable excipients.

Said excipients are selected depending on the pharmaceutical formulation and the desired route of administration.

In the pharmaceutical compositions of the invention, designed for oral, sublingual, subcutaneous, intramuscular, intravenous, local, intratracheal, intranasal, transdermal or rectal administration, the active ingredients of the above formula (I) or any salt thereof may be administered to animals and human beings in single dose mixed with conventional pharmaceutical carriers for the treatment or prophylaxis of the above disorders or pathologies.

Suitable single-dose forms of administration comprise oral forms such as tablets, gelatin capsules, powders, granules, oral solutions or suspensions, as well as forms for sublingual, buccal, intratracheal, intranasal administration, forms for subcutaneous, intramuscular or intravenous administration and forms for rectal administration.

For local administration, the compounds of the invention may be formulated as creams, ointments or lotions.

In order to ensure the desired prophylactic or therapeutical effect, the dosage of active ingredient may vary from 0.01 to 50 mg per kg of body weight and per day.

Each single dose may comprise from 0.5 to 1000 mg, preferably from 1 to 500 mg of active ingredient in association with a pharmaceutical carrier. Said unit dose may be administered 1 to 5 times per day so as to administer from 0.5 to 5000 mg per day, preferably from 1 to 2500 mg.

Where a solid composition is prepared, such as tablets, the main active ingredient is mixed with a pharmaceutical carrier such as gelatin, starch, lactose, magnesium stearate, talc, gum-arabic and the like; tablets may be coated with sucrose, a cellulose derivative or other suitable materials or alternatively they may be treated in such a way that they have sustained or delayed activity and release a predetermined amount of active ingredient continuously.

A preparation in gelatin capsules is obtained by mixing the active ingredient with a diluent and poring the resulting mixture in soft or hard gelatin capsules.

A preparation in the form of a syrup or elixir as well as preparations for the administration of drops may contain the active ingredient together with a sweetener preferably one having negligible calorific value, methylparaben and propylparaben as antiseptic agent as well as a flavouring agent and a suitable colouring.

The water-dispersible powders or granules may contain the active ingredient in admixture with dispersing agents, wetting agents, suspending agents such as polyvinylpyrrolidone, as well as sweeteners or flavour correctors.

For the rectal administration, suppositories are used which are prepared with binding agents which melt at rectal temperature such as cocoa butter or polyethylene glycols.

For parenteral administration, aqueous suspensions, isotonic saline solutions or sterile injectable solutions are used containing pharmaceutically acceptable dispersing agents and/or wetting agents such as propylene glycol or butylene glycol.

The active ingredient may also be formulated in the form of microcapsules, where appropriate with one or more carriers or additives.

The compositions of the invention may contain together with the compounds of the above formula (I) or a pharmaceutically acceptable salt thereof, other active ingredients which may be useful for the treatment of the above mentioned disorders or pathologies.

The compounds in which $Z_1$ represents a $(C_4-C_9)$-alkylene and $Q_1$ is bonded to $Z_1$ via a nitrogen atom and represents an amino, guanidino or amidino group, whether they are substituted or otherwise, are particularly preferred; on the other hand, the compounds in which $NR_3R_4$ represents pyrrolidinyl are preferred.

Compounds (I) in which $Z_1$ represents methylenecyclohexylmethylene, $Q_1$ represents amino, alkylamino or dialkylamino, $R_3$ and $R_4$ form with the nitrogen atom to which they are bound pyrrolidinyl, $Ar_2$ represents phenyl or methoxyphenyl, $Ar_1$ represents naphthyl and $Q_2$, $Q_3$ $R_1$, $R_2$ and $R'_2$ are such as defined in (I) are more particularly preferred.

In the following text, examples of the compounds of the invention and preparation processes are described. First, the preparation of a number of intermediate compounds for synthesis is indicated by way of illustration.

The compounds of formula I contain in general two asymmetric carbons and can be isolated in the form of a mixture of two diastereoisomeric racemic pairs whose relative proportions will depend on the operating conditions, given their different physical properties. When the starting materials which contain an asymmetric carbon are not racemic mixtures but are enriched with one or the other of the enantiomers, the final product will in general not be a mixture of two racemates except if the operating conditions result in racemization.

In the products of formula I described hereinafter, the relative proportions of the two racemic pairs are measured by conventional methods such as high-performance liquid chromatography or nuclear magnetic resonance spectroscopy.

Unless otherwise stated, the isolated nitriles of formula II are an equimolar mixture of diastereoisomers.

A—Preparation of sulphonamides

N-(2-naphthylsulphonyl)-1,2,3,4-tetrahydroisoquinoline-3-carboxylic acid.

46.8 ml of a N aqueous NaOH solution are introduced into a suspension of 5 g of 1,2,3,4-tetrahydroiso-quinoline-3-carboxylic acid hydrochloride in 150 ml of dioxane followed, slowly, by 5.3 g of 2-naphthalene-sulphonyl chloride and a N NaOH solution in order to maintain a pH in the vicinity of 10. At the end of the addition, the mixture is kept stirring for 3 hours at around 20° C. before the addition of 150 ml of $CH_2Cl_2$. After acidification of the aqueous phase up to pH 2, the organic phase is separated and the aqueous phase is reextracted with 150 ml of $CH_2Cl_2$. The organic phases are dried, concentrated and the residue is purified by silica gel chromatography, eluting with a mixture of methylene chloride and methanol (80/20-V/V). 7 g of sulphonamide are obtained in the form of a hemihydrate, m.p.=110° C.

N-(3,4-dichlorophenylsulphonyl)-O-methyltyrosine.

5 g of 3,4-dichlorophenylsulphonyl chloride are introduced, with stirring, into a mixture of 3,8 g of ethyl O-methyltyrosinate in 35 ml of $CH_2Cl_2$ and 50 ml of a saturated aqueous potassium carbonate solution. After one night, the solid is removed, the organic phase separated and the aqueous phase reextracted with $CH_2Cl_2$. The dried organic phases are concentrated and the residue is chromatographed on a silica column, eluting with a mixture of $CH_2Cl_2$ and $CH_3OH$ (95/5-V/V). 6.8 g of racemic ethyl N-(3,4-dichlorophenylsulphonyl)-O-methyltyrosinate are obtained, which product melts at 99° C. This ester is hydrolysed in 100 ml of $C_2H_5OH$ containing 9.5 ml of a 5N aqueous KOH solution to give, after acidification, 5.5 g of the corresponding acid which melts at 183° C.

The following are prepared in the same manner:

N-(2-naphthylsulphonyl)phenylalanine m.p.=146° C. (methyl ester: m.p.=144° C.)

N-(2-naphthylsulphonyl)-O-methyltyrosine m.p.=174° C. (ethyl ester: m.p.=138° C.)

N-methyl-N-(2-naphthylsulphonyl)phenylalanine m.p.=122° C. (methyl ester: m.p.=106° C.)

N-(2-naphthylsulphonyl)-2-amino-2-indancarboxylic acid m.p.=264° C.

N-(5-isoquinolylsulphonyl)-alpha-methylphenylalanine (ethyl ether m.p.=60° C.)

N-(8-quinolinylsulphonyl)-O-methyltyrosine m.p.=228° C.

N-(2-naphthylsulphonyl)-O-benzyltyrosine m.p.=182° C.

N-(1-naphthylsulphonyl)-2,4-dimethylphenylalanine m.p.=220° C.

(ethyl ester: m.p.=134° C.)

N-(4-tolylsulphonyl)-4-chlorophenylalanine m.p.=164° C.

(ethyl ester m.p.=114° C.

The starting ethyl 2-amino-2-indancarboxylate can be prepared from ethyl N-diphenylmethyleneglycinate: at −70° C., 25 g of ethyl N-diphenylmethyleneglycinate are introduced into 1500 ml of tetrahydrofuran containing 10.5 g of potassium tert-butoxide, followed, slowly, by 12.6 ml of α,α-(dibromo)-ortho-xylene and, after 12 hours, by 10.5 g of potassium tert-butoxide. The mixture is allowed to return to room temperature and after 12 hours, a saturated aqueous $NH_4Cl$ solution is introduced into the medium. The solvents are removed by distillation under reduced pressure and the residue is extracted with $(C_2H_5)_2O$. The separated organic phase is stirred for 16 hours, at room temperature, with 150 ml of a N aqueous HCl solution. The aqueous solution, after 3 washes with $(C_2H_5)_2O$, is adjusted to pH 8 by addition of $NaHCO_3$ and 13.4 g of the desired ester are extracted therefrom in $CH_2Cl_2$.

m.p.=56° C.

B. Preparation of (4-cyano)phenylalanylamides

1. Ethyl ester of (4-cyano)phenylalanine.

7.23 g of tetrabutylammonium bromide, 93 g of $Na_2CO_3$ and then 60 g of ethyl N-(diphenylmethylene)glycinate are introduced into a solution of 40.4 g of 4-(bromomethyl) benzonitrile in 460 ml of anhydrous $CH_3CN$. The medium is maintained for 4 hours at its reflux temperature and then the solids are separated and the solvents removed by distillation under reduced pressure. The residue is taken up in 1 liter of $(C_2H_5)_2O$ and then, after filtration, concentrated to 500 ml before adding 300 ml of a N aqueous HCl solution to it. After stirring for 16 hours, the mixture is decanted and the pH of the separated aqueous phase is adjusted to around 8. The final product is extracted therefrom in $CH_2Cl_2$. 34.8 g of ester are obtained in an oily form of which the hydrochloride melts at 170° C.

2. Separation of the laevorotatary and dextrorotatory isomers of the preceding ester by enzymatic hydrolysis.

10 g of racemic ester, 20 mg of alpha-chymotrypsin and 0.9 g of bovine serum albumin are stirred for 16 hours at around 25° C., in 1 l of a 0.1 M aqueous $CH_3COONa$ solution whose pH is adjusted to between 6.5 and 6.8 by addition of a 0.1 N aqueous NaOH solution. After filtration of the medium on talc and then on activated carbon, half of the solvent is removed by distillation under reduced pressure at around 35° C. and the remaining aqueous solution is adjusted to pH 8 by addition of NaOH, and then extracted with $CH_2Cl_2$. After the usual treatments of the organic phase, 4.5 g of oily laevorotatary ethyl 2-amino-3-(4-cyanophenyl)propionate are obtained.

$[\alpha]_D^{20} = -27°$ C. (c=1;$CH_3OH$)

The basic aqueous solution contains the sodium salt of the acid corresponding to the other enantiomer. After acidification up to pH 4 followed by freeze-drying, a white powder is isolated which contains the laevorotatary amino acid.

3. N-(t-butoxycarbonyl)-4-cyanophenylalanine.

20 ml of N aqueous NaOH solution and 4.34 g of di-(tert-butyl)carbonate are introduced at 5° C. into a solution of 4.34 g of an ethyl ester of 4-cyanophenyl-alanine in 70 ml of dioxane. After returning to room temperature and 3 hours of stirring, the reaction medium is concentrated to dryness; 100 ml of water is then poured over the residue and after washing with CH$_3$COOC$_2$H$_5$, the aqueous solution is adjusted to pH 2 by addition of a KHSO$_4$ solution; the final product is then extracted from CH$_2$Cl$_2$.

4. 1-[2-amino-3-(4-cyanophenyl)]propionylpyrrolidine.

1.98 g of pyrrolidine and 3 g of hydroxybenzotriazole are introduced, at 0° C., into 70 ml of CH$_2$Cl$_2$ containing 5.4 g of N-(t-butoxycarbonyl)-4-cyanophenyl-alanine, followed at around −5° C. by a solution of 4 g of dicyclohexylcarbodiimide in 30 ml of CH$_2$Cl$_2$. After stirring for 16 hours at 20° C., the organic phase is filtered and washed with a saturated aqueous Na$_2$CO$_3$ solution and then with a KHSO$_4$ solution of pH 2 and finally with water. After the usual treatments, 4.73 g of the desired derivative is obtained whose primary amine group is protected by a t-butoxycarbonyl group; this group can be removed by the action of an acid: the compound is dissolved in 50 ml of ethyl acetate and 50 ml of an ethyl acetate solution saturated at 15° C. with HCl are added at around 0° C.; after stirring for 2 hours at around 20° C., the solvent is removed and the hydrochloride of the desired product is obtained.

The racemic hydrochloride melts at 224° C.

The enantiomer, prepared from the laevorotatary ester, is laevorotatary:

$[\alpha]_D^{20} = -68°8$ (c=1; CH$_3$OH)

whereas that prepared from the laevorotatary residual amino acid is dextrorotatory, under the same measurement conditions.

5. 1-[2-amino-3-(4-cyanophenyl)]propionyl piperidine.

The racemic hydrochloride melts at 218° C.; the intermediate compound N-(t-butoxycarbonyl) melts at 132° C.

6. [N-methyl-N-ethyl]-2-amino-3-(4-cyanophenyl)-propionamide.

The racemic hydrochloride melts at 228° C.

C. Preparation of the compounds of formula II

1. By reaction of a sulphonamide and a (4-cyano)-phenylalanylamide.

1-(2-[2-(3,4-dichlorophenylsulphamoyl)-3-(4-methoxyphenyl)propionamido]-3-(4-cyanophenyl)propionyl) pyrrolidine (compound 1)

with a CH$_2$Cl$_2$/CH$_3$OH mixture (98/2-V/V). 2.9 g of a mixture of diastereoisomers of the nitrile are obtained, which mixture melts at 101° C.

The following are obtained in the same manner:

N-ethyl-N-methyl-2-[2-(3,4-dichlorophenylsulphamoyl)-3-(4-methoxyphenyl)propionamido]-3-(4-cyanophenyl) propionamide (compound 2).

m.p.=192° C., crystallized with 1.5 H$_2$O 1-(2-[2-(2-naphthylsulphamoyl)-3-(4-methoxyphenyl)-propionamido]-3-(4-cyanophenyl)propionyl)pyrrolidine (compound 3)

Prepared from racemic sulphonamide and laevorotatary 1-[2-amino-3-(4-cyanophenyl) propionyl]-pyrrolidine hydrochloride.

m.p.=135° C., crystallized with 1.5 H$_2$O 1-(2-[2-(2-naphthylsulphamoyl)-3-phenylpropionamido]-3-(4-cyanophenyl)propionyl)pyrrolidine (compound 4)

m.p.=206° C., crystallized with H$_2$O 1-(2-[2-(2-naphthylsulphamoyl)-3-phenylpropionamido]-3-(4-cyanophenyl)propionyl)piperidine (compound 5)

m.p.=210° C., crystallized with H$_2$O

N-ethyl-N-methyl-2-[2-(1-naphthylsulphamoyl)-3-(3,4-dichlorophenyl)propionamido]-3-(4-cyanophenyl) propionamide (compound 6).

m.p.=182° C., crystallized with 0.5 H$_2$O

N-(2-naphthylsulphonyl)-3-[1-(pyrrolidinylcarbonyl)-2-(4-cyanophenyl)ethylaminocarbonyl]tetrahydroisoquinoline (compound 7)

m.p.=232° C., crystallized with 0.75 H$_2$O 1-(2-[(2-(2-naphthylsulphamoyl)-2-indanyl)carboxamido]-3-(4-cyanophenyl)propionyl)piperidine (compound 8)

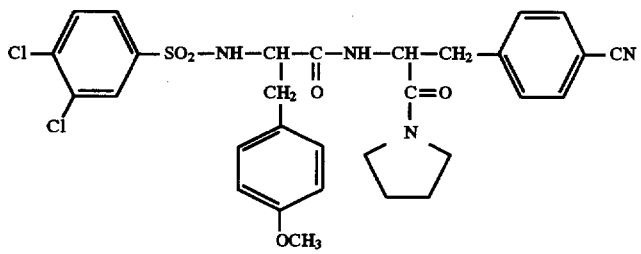

2.5 g of N-(3,4-dichlorophenylsulphonyl)-O-methylthyrosine, 1,82 g of 1-[2-amino-3-(4-cyano)phenyl-propionyl]pyrrolidine hydrochloride and 2.87 g of benzotriazol-1-yloxy-tris(dimethylamino)phosphonium hexafluorophosphate (BOP) are introduced into 100 ml of acetonitrile, at 0° C., followed by 1.75 ml of triethylamine at a temperature of less than 5° C. After stirring for 16 hours at room temperature at around 20° C., the solvent is removed under reduced pressure and the residue is dissolved in 80 ml of CH$_3$COOC$_2$H$_5$. After washing the organic phase with an aqueous solution at pH 2, with a saturated NaHCO$_3$ solution and with water, the solvent is removed by distillation and the residue is chromatographed on a silica gel column, eluting m.p.=224° C., crystallized with H$_2$O

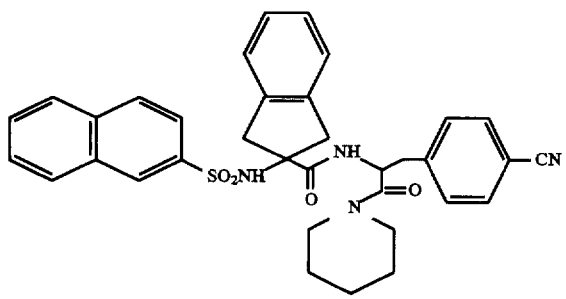

1-(2-[2-(8-quinolylsulphamoyl)-3-(4-methoxyphenyl) propionamido]-3-(4-cyanophenyl)propionyl)pyrrolidine (compound 9) prepared from the racemic sulphonamide and the laevorotatary 1-[2-amino-3-(4-cyanophenyl)] propionylpyrrolidine hydrochloride m.p.=175° C., crystallized with 1.5 H$_2$O 1-(2-[2-(2-naphthylsulphamoyl)-3-(4-benzyloxyphenyl)-propionamido]-3-(4-cyanophenyl)propionyl)pyrrolidine (compound 10)

m.p.=110 ° C., crystallized with 1 H$_2$O

2. By a coupling reaction of an alpha-amino acid with a (4-cyanophenyl)alanylamide followed by reaction with the sulphochloride.

2.1. 1-(2-[2-(2-naphthylsulphamoyl)-3-phenylpropionamido]-3-(4-cyanophenyl)propionyl) pyrrolidine (compound 4 and compound 4A).

a) 1.75 g of N-(t-butoxycarbonyl)phenylalanine, 0.95 ml of N-ethylmorpholine, 3.34 g of BOP and 1.75 g of 1-(2-amino-3-(4-cyanophenyl)propionyl)pyrrolidine hydrochloride are introduced, at 0° C., into 20 ml of CH$_3$CN, followed by 1.6 ml of N-ethylmorpholine. After stirring for 16 hours at room temperature, the solvent is removed by distillation under reduced pressure and the residue is dissolved in CH$_3$COOC$_2$H$_5$, in the presence of a saturated NaHCO$_3$ solution. The organic phase, washed in the usual manner and dried, is concentrated under reduced pressure and the residue is purified by chromatography on a silica gel column, eluting with CH$_2$Cl$_2$/CH$_3$OH (98/2-V/V).

The product obtained is dissolved in 50 ml of CH$_2$Cl$_2$ and, at 0° C., 50 ml of CF$_3$COOH are added. When the medium has returned to room temperature, it is stirred for another 30 minutes and then the volatile products are removed by distillation under reduced pressure; after addition of 40 ml of water, the mixture is freeze-dried to give 2.9 g of trifluoroacetate.

b) 1.75 ml of N-ethylmorpholine are slowly introduced, at 0° C., into 35 ml of a solution of 2.3 g of the preceding trifluoroacetate in CH$_2$Cl$_2$, followed by 1.1 g of 2-naphthalenesulphonyl chloride in solution in 10 ml of CH$_2$Cl$_2$. After stirring for 4 hours at room temperature, the organic phase is washed with a 0.1 N aqueous HCl solution and then with water. The residue obtained after distillation of the solvent is chromatographed on silica gel, eluting with a CH$_2$Cl$_2$/CH$_3$OH mixture (95/5-V/V) to give 1.95 g of the expected compound 4.

When the two starting materials are pure enantiomers, only one of the four stereoisomers of compound 4 is obtained under these conditions.

The product (compound 4A) prepared from the two laevorotatary enantiomers previously described, crystallized with 0.25 H$_2$O, melts at 118° C.

[α]$_D^{20}$=−19°5 C. (c=1; DMSO)

The following are obtained by the same reaction sequence:

starting with N-(t-butoxycarbonyl)-L-phenylalanine and the hydrochloride of laevorotatory 1-[2-amino-3-(4-cyanophenyl)propionyl]pyrrolidine, the compound 4B.

[α]$_D^{20}$=+15°5 C. (c=1 DMSO)

starting with N-(t-butoxycarbonyl)-O-methyl-D-tyrosine and the hydrochloride of laevorotatory 1-[2-amino-3-(4-cyanophenyl)propionyl]pyrrolidine, hydrated 1-(2-[2-(2-naphthylsulphamoyl)-3-(4-methoxyphenyl) propionamido]-3-(4-cyanophenyl)propionyl)pyrrolidine (compound 3A)

m.p.=143° C.

[α]$_D^{20}$=+4°1 C. (c=1; CH$_3$OH)

starting with N-(t-butoxycarbonyl)-D-phenylalanine and the hydrochloride of dextrorotatory 1-[2-amino-3-(4-cyanophenyl)propionyl]pyrrolidine, 1-(2-[2-(5-dimethylamino-1-naphthylsulphamoyl)-3-phenylpropionamido]-3-(4-cyanophenyl)propionyl) pyrrolidine (compound 11)

m.p.=116° C.

[α]$_D^{20}$=−4°5 (c=1; DMSO)

starting with the racemic mixtures, 1-(2-[2-(1-naphthylsulphamoyl)-3-(2-thienyl)propionamido]-3-(4-cyanophenyl)propionyl)pyrrolidine (compound 12)

m.p.=121° C.

2.2. 1-(2-[(N-(2-naphthylsulphamoyl)-5-methoxy-2-indolyl)carboxamido]-3-(4-cyanophenyl)propionyl) pyrrolidine (compound 13).

a) 1.3 g of 5-methoxy-2-indolecarboxylic acid, 3.16 g of BOP and 2 g of 1-(2-amino-3-(4-cyanophenyl)propionyl) pyrrolidine hydrochloride are introduced, at 0° C., into 100 ml of CH$_3$CN, followed by 2.5 ml of triethylamine.

After stirring for 16 hours at room temperature, 1-(2-[(5-methoxy-2-indolyl)carboxamido]-3-(4-cyanophenyl) propionyl)pyrrolidine is filtered, washed with ether and dried.

m.p.=204° C.

b) 0.23 g of a 60% suspension of sodium hydride in oil is added, at 0° C., to a suspension of 2.2 g of the preceding product in 100 ml of THF.

After stirring for 1 hour at 5° C., 1.3 g of 2-naphthalenesulphonyl chloride in solution in 20 ml of THF are added at around 0° C. and the mixture is stirred at room temperature for 16 hours and then at around 50° C. for 3 hours. The precipitate is filtered and the filtrate is evaporated under reduced pressure. The residue is chromatographed on a silica column, eluting with CH$_2$Cl$_2$/cyclohexane (70/30-V/V) to give the expected hemihydrate product which melts at 186° C.

In the same manner, starting with 2-indolecarboxylic acid, 1-(2-[(N-(2-naphthylsulphamoyl)-2-indolyl)carboxamido]-3-(4-cyanophenyl)propionyl)pyrrolidine is isolated (compound 14)

m.p.=180° C.

3. By substitution of a sulphonamide of formula II in order to obtain a compound in which R$_2$ is different from H.

1-(2-[2-(N-methyl-2-naphthylsulphamoyl)-3-phenylpropionamido]-3-(4-cyanophenyl)propionyl) pyrrolidine (compound 15)

2 g of compound 4 are dissolved in 20 ml of dimethylformamide at 0° C. and 0.475 g of K$_2$CO$_3$ and 0.214 ml of $ICH_3$ are added. After 24 hours at 5° C., 20 ml of $H_2O$ and 40 ml of $CH_2Cl_2$ are added. The organic phase decanted is washed, dried and concentrated to dryness. The residue is recrystallized from $(CH_3)_2CHOH$ to give 1.76 g of final product which melts at 186° C.

The enantiomer prepared from compound 4A described in C-2 is dexrorotatory.

$[\alpha]_D^{20} = 40°$ C. (c=1; $CH_3OH$)

4. By reaction of a sulphonamide and an ester of 4-cyanophenylalanine followed by a saponification and an acylation.

1-(2-[2-(4-methylphenylsulphamoyl)-3-(4-chlorophenyl) propionamido]-3-(4-cyanophenyl)propionyl) hexahydroazepine (compound 16).

a) 4 g of N-(4-tolylsulphonyl)-4-chlorophenyl)alanine and 4.1 g of 4-cyanophenylalanine ethyl ester hydrochloride are reacted under the conditions described in § (C.1) and 3.7 g of ethyl 2-(2-(4-tolylsulphamoyl)-3-(4- chlorophenyl) propionamido)-3-(4-cyanophenyl)propionate which melts at 82° C. are obtained by the usual treatments.

This ester is hydrolysed by a solution of 1 g of KOH in a mixture of 10 ml of water and 20 ml of ethanol to give, after acidification, 2.5 g of the corresponding acid which melts at 104° C. b) 2 g of B.O.P. and 1.6 ml of N-ethylmorpholine are added, at 0° C., to a solution of 2.5 g of the preceding acid in 80 ml of $CH_3CN$, followed by 0.5 g of hexamethyleneimine. After stirring for 16 hours at around 20° C., the solvent is evaporated. The residue is dissolved in $CH_2Cl_2$. The organic phase is washed in the usual manner, dried and then concentrated under reduced pressure.

After silica gel chromatography, eluting with a $CH_2Cl_2/CH_3OH$ mixture (V/V:95/5), 1.3 g of the expected product is obtained.

m.p.=194° C.

(2-[2-(1-naphthylsulphamoyl)-3-(2,4-dimethylphenyl) propionamido]-3-(4-cyanophenyl)propionyl)dimethylamine hemi-hydrated (compound 17) is prepared in the same manner.

m.p.=140° C.

D. Preparation of imidoesters, intermediates in the preparation of amidines from the nitriles 1. Starting with compound 5 are $C_2H_5OH$.

2 g of compound 5 are rapidly introduced into 20 ml of anhydrous $C_2H_5OH$ saturated at 0° C. with HCl. After stirring overnight, at a temperature of between 0° C. and 5° C., the solvent is removed by distillation at a temperature of less than 25° C., to yield the hydrochloride of the desired product.

2. Starting with compound 4 and $CH_3OH$.

5 g of compound 4 are rapidly introduced into 100 ml of anhydrous $CH_3OH$ saturated at 0° C. with HCl. After stirring overnight at around 0° C., the solvent is removed by distillation at a temperature of less than 22° C., in order to isolate the hydrochloride of the imidoester.

In order to obtain the corresponding base, the hydrochloride is dissolved in 100 ml of $CH_2Cl_2$ and then triethylamine is added at around 5° C. until a pH of 7.5 (measured in aqueous medium) is obtained. The organic phase is then washed 5 times with 30 ml of water at around 20° C., dried and concentrated to give 5.2 g of imidoester.

The structural formulae and the physico-chemical characteristics of the products prepared as described in the following examples are presented in Table I; A/B represents the relative proportions of the 2 racemates.

EXAMPLE 1

2 g of the hydrochloride of the imidoester of compound 5, prepared according to D-1, are dissolved in 20 ml of anhydrous isopropanol and 1.6 ml of n-propylamine are introduced into the solution. After stirring for 2 hours, the solvent is removed and the residue is chromatographed on silica gel, eluting with a $CH_2Cl_2/CH_3OH$ mixture (9/1-V/V). 1.7 g of the hydrochloride of the expected product are thus obtained.

EXAMPLE 2

1 g of the hydrochloride of the imidoester of compound 5, prepared according to D-1, are dissolved in 10 ml of anhydrous $C_2H_5OH$. 0.14 ml of 1,2-ethanediamine is added and the medium is maintained at around 70° C. for 1 hour 30 minutes. The solvent is removed under reduced pressure and the residue is purified by silica gel chromatography, eluting with a $CH_2Cl_2/CH_3OH$ mixture (92/8-V/V).

EXAMPLE 3

2.1 ml of triethylamine and 0.33 ml of 1-aminopentanol are added, at 5° C., to a solution of 2 g of the hydrochloride of the imidoester of compound 4, prepared according to D-1. After stirring for 16 hours at room temperature, the solvent is evaporated under reduced pressure and the residue is chromatographed on silica gel, eluting with a $CH_2Cl_2/CH_3OH$ mixture (9/1-V/V) to yield 1.5 g of hydrochloride.

EXAMPLE 4

3.5 ml of triethylamine and 2.2 g of N-(t-butyloxycarbonyl)-1,3-propanediamine are introduced, at 5° C., into a solution of 4.5 g of the hydrochloride of the imidoester of compound 4. After 20 hours at room temperature, the solvent is removed by distillation under reduced pressure and the residue is dissolved in 50 ml of $CH_2Cl_2$. The organic solution is washed with a 0.1 N aqueous NaOH solution, and then with water and dried. The residue obtained after concentration crystallizes from a mixture of $[(CH_3)_2CH]_2O$ and $CH_3COOC_2H_5$ to give 2.5 g of the desired product.

EXAMPLE 5

40 ml of $CH_3COOC_2H_5$, saturated with HCl, are introduced, at 5° C., into a solution of 4 g of the product obtained in Example 4 in 40 ml of $CH_3COOC_2H_5$. After 2 hours at around 20° C., the precipitate is isolated, washed with $CH_3COOC_2H_5$ and then dissolved in a mixture of 40 ml of $CH_2Cl_2$ and 20 ml of 0.5 N aqueous NaOH solution. After stirring for 16 hours at around 20° C., the organic phase is separated and it is treated in the usual manner to yield 2.1 g of the expected product after recrystallization from a mixture of $CH_3COOC_2H_5$ and $CH_3OH$.

EXAMPLE 6

2 g of the imidoester of compound 4A, prepared according to D-2, are introduced into 30 ml of anhydrous $CH_3OH$ and 0.82 g of trans-4[N-(t-butoxycarbonyl)aminomethyl] cyclohexylmethylamine is added followed by a few drops of $CH_3OH$, saturated with HCl, until a pH of 8 (measured in water) is obtained.

After 52 hours at room temperature, the $CH_3OH$ is evaporated, 30 ml of $CH_2Cl_2$ are added to the medium, and then it is removed under reduced pressure; the residue obtained is introduced, at 5° C., into 30 ml of $CH_3COOC_2H_5$, saturated at 15° C. with HCl. After returning to room temperature, it is kept stirring for half an hour and then the solvent is removed before purifying the residue by silica gel chromatography, eluting with a $CH_2Cl_2/CH_3OH$ mixture (80/20-V/V).

After recrystallization from 1-propanol, 1.8 g of the product mentioned in Table I are isolated.

EXAMPLE 7 a) (N,N-dimethyl)-4-[aminomethyl] cyclohexylmethylamine (trans)

63.6 ml of an N aqueous NaOH solution and 1.28 g of MgO are introduced, at 0° C., into 50 ml of dioxane containing 5 g of trans-4-(aminomethyl) cyclohexylcarboxylic acid, followed, slowly, by 6.94 g of di(t-butyl)carbonate in solution in 20 ml of dioxane. After 20 hours at room temperature, the mixture is filtered, the solvent is removed and the residue is taken up in 100 ml of $H_2O$ and the aqueous phase is washed with $(C_2H_5)_2O$ before acidifying it up to pH 2 by addition of $KHSO)_4$; it is then extracted in $CH_3COOC_2H_5$ to yield 7.3 g of trans-N-(t-butoxycarbonyl)-4-(aminomethyl)cyclohexylcarboxylic acid which melts at 125° C.

This compound is then dissolved in a mixture of 20 ml of $CH_2Cl_2$ and 25 ml of $(CH_3)_2NCHO$, into which 4.8 g of hydroxybenzotriazole are introduced, followed by 6.15 g of N,N'-dicyclohexylcarbodiimide in solution in 50 ml of $CH_2Cl_2$. After stirring for 2 hours, 4 g of anhydrous $(CH_3)_2NH$ are added and the mixture is kept stirring for 16 hours. The precipitate is then separated, the organic phase is washed several times with a saturated aqueous $NaHCO_3$ solution and then with water. After drying, concentration and chromatography of the residue on a silica gel, eluting with $CH_3COOC_2H_5$, 5.8 g of trans-N,N-dimethyl-N'-(t-butoxycarbonyl)-4-(aminomethyl) cyclohexylcarboxamide are isolated, which product melts at 94° C.

This compound is dissolved in 50 ml of $CH_3COOC_2H_5$ saturated with HCl and after one hour, the hydrochloride precipitate which appears is filtered, which precipitate, when treated with a base, gives 3.5 g of trans-N,N-dimethyl-4-(aminomethyl)cyclohexylcarboxamide in the form of an oil.

This oil is dissolved in 10 ml of tetrahydrofuran into which 25 ml of 1M $LiAlH_4$ solution in the same solvent are then introduced at 0° C. After stirring for 16 hours at room temperature, the mixture is cooled to 0° C. and 0.9 ml of ice-cold water is added followed by 2.7 ml of a 15% (w/V) aqueous NaOH solution and finally by 0.9 ml of water. The precipitate is removed and the solvent is evaporated by distillation under reduced pressure to give the expected diamine which distils at 60° C. under 1 Pa.

b) By reacting trans-(N,N-dimethyl)-4-(aminomethyl) cyclohexylmethylamine and the imidoester of compound 4A, according to the procedure described in Example 3, the pure enantiomer described in Table I is obtained after recrystallization from isopropanol.

Preparation of the compound of Example 46 from that of Example 38

0.08 g of aminoiminomethanesulphonic acid and 0.1 ml of triethylamine are added, under an inert atmosphere, to a solution of 0.5 g of compound 38 in 10 ml of anhydrous methanol. After 16 hours at about 20° C., the solvent is evaporated and the residue is taken up in 20 ml of 1N aqueous NaOH solution at a temperature in the vicinity of 0° C. and extracted with dichloromethane. The organic phase is dried, concentrated and the residue is chromatographed on a silica column, eluting with di-chloromethane/methanol (9/1-V/V) and then with a methanol/aqueous solution of concentrated $NH_4OH$ mixture (7/3-V/V). After recrystallization from an ethanol/ethyl acetate mixture (8/2-V/V), the expected product is isolated in the form of a base whose dihydrochloride is prepared by the action of HCl in ethanol.

m.p.=185° C. (2 HCl, $H_2O$).

Following the general procedure described in example 3, and starting from the appropriate amines, compound 20 is prepared from compound 4A, compound 60 is prepared from compound 4B, compound 58 is prepared from compound 3A, compound 64 is prepared from compound 10.

Following the procedure described in example 6 and starting from the appropriate amines compounds 45, 47 and 48 are prepared from compound 4A.

EXAMPLE 61 a) N-(butyloxycarbonyl)-4-(aminomethyl) cyclohexylmethylamine (cis).

1.6 g of potassium tert-butoxide are added, at 0° C., in portions, to a solution of 2 g of cis-1,4-[dimethylamino] cyclohexane dihydrochloride (obtained according to the method described in Ber. 71 B, 759 (1938)) in 70 ml of anhydrous methanol, followed by a solution of 2.1 g of di-tert-butyl dicarbonate in 100 ml of methanol.

The mixture is heated for 16 hours at around 35° C., the precipitate is filtered and the solvent is evaporated under reduced pressure. The expected product is isolated by silica column chromatography, eluting with $CH_2Cl_2$/MeOH: 95/5 followed by 80/20 (V/V)

m.p.=201° C.

b) By reacting the preceding amine with 2 g of the imidoester of compound 4A prepared according to D-2 under the conditions described in Example 6, the expected product is obtained which is dissolved in 15 ml of HCl, filtered and then extracted from the aqueous phase with 3 times 7 ml of butanol. The solvent is evaporated under reduced pressure. The residue is taken up in water and freeze-dried to give the pure enantiomer described in Table I.

EXAMPLE 67 a) 4(N,N-dimethylaminomethyl)cyclohexylmethylamine, cis

-cyclohexyl-1,4-dimethanol, cis 328 ml of a 1M solution of $LiAlH_4$ in tetrahydrofurane are added slowly, at 0° C., to a solution of 66 g of ethyl cyclohexyl-1,4-dicarboxylate, cis in 500 ml THF.

The mixture is stirred for 16 hours at room temperature and then cooled at about 0° C. 13 ml of water, 39 ml of an aqueous solution of 15% NaOH (w/w) and then 13 ml of water are successively added to the mixture.

Salts are filtered out, the solvent is evaporated under pressure and the residue is distilled at 120°–124° C. under $45.10^{-6}$ bar(4.5 Pa.) 37 g of the expected product are obtained.

-cyclohexyl-1-4-diparatoluene sulfonate (cis)

A solution of 41 g of paratoluene sulfonyl chloride and 28 ml triethylamine in 35 ml tetrahydrofurane are added, at 0° C., to a solution of the preceding alcohol in 70 ml of tetrahydrofurane.

The mixture is stirred at 25° C. for 24 hours and next heated at 50° C. for 3 hours.

After cooling, 50 ml of a saturated NaCl solution and 50 ml of a HCl solution about 1N are added to the reaction mixture. The solvent is evaporated under pressure and the residue is taken up in 300 ml ether and 200 ml 2N NaOH and the resulting mixture is kept stirring for 16 hours at room temperature.

After decantation the aqueous phase is extracted with dichloromethane. The organic phases are dried and the solvent is removed by distillation under pressure. 29 g of the expected product are finally isolated.

F=91° C.

-4-(N,N-dimethylaminomethyl)cyclohexylmethylamine, cis 14 g of the preceding ditosylate are stirred at 25° C. for 48 hours in an autoclave in a methanolic solution saturated with ammonia. After evaporation under reduced pressure, the residue is taken up in $CH_2Cl_2$ and 1N, HCl.

The resulting mixture is decanted and the aqueous phase is basified with 2N, NaOH and then extracted with dichloromethane. After evaporation under reduced pressure, the residue is purified by silica gel chromatography, eluting with a $CH_2Cl_2/CH_3OH$ mixture (70/30 - v/v) 6 g of 4-aminomethylcyclohexyl paratoluene sulfonate, cis are isolated.

The preceding tosylate is then added to a saturated solution of dimethylamine in methanol and then heated at 70° C. for 20 hours in an autoclave.

After evaporation under reduced pressure, the residue is taken up in $CH_2Cl_2$ and 2 ml of water. 2 g of solid KOH are added to the mixture.

The organic phase is then dried and then concentrated under vacuum. The hydrochloride salt is formed and the expected dihydrochloride which melts at 252° C. is isolated after recrystallization from ethanol.

b) compound 67

0.9 g of the preceding of the dihydrochloride are reacted with 2.4 g of the dihydrochloride of the imidoester of compound 4A and 1.2 ml of N-ethylmorpholine in 100 ml methanol. The mixture is stirred at 40° C. for 16 hours, the solvent is then evaporated and the pur enantiomer described in Table I is obtained after treatment according to the procedure described in example 61 § b.

EXAMPLE 69

(Case where $R_2$ and $R'_2$ form a double bond)
1-(2-[N-(2-naphthylsulfamoyl)-2-indolylcarboxamido]-3-(4-(N-[4-(dimethylaminomethyl)-trans-cyclohexylmethyl]-amidino)phenyl)propionyl)pyrrolidine, dihydrochloride, $4H_2O$.

This compound is prepared from compound 14 according to the general procedure described in Example 1.

m.p.=230° C.

EXAMPLE 70

1-(2-[(N-(2-naphthylsulphamoyl)-5-methoxy-2-indolyl)carboxamido]-3-(4-(N-[4-(dimethylaminomethyl)-trans-cyclohexylmethyl]amidino)phenyl)propionyl)pyrrolidine.

This compound is prepared in the same manner from compound 13.

m.p.=230° C.

Compound 18:
1-(2-[2-(5-isoquinolylsulfamoyl)-2-methyl-3-phenyl-propionamido]-3-(4-cyanophenyl)-propionyl)-pyrrolidine.

m.p.=264° C.

This compound is prepared as for compound 16 (see § C.4).

TABLE 1

$$Ar_1-SO_2-N(R_1)-C(R_2)(H)-C(=O)-N(H)-CH(CH_2Ar_2)-C(=O)-N(R_3)(R_4)$$

with para-substituted phenyl: $C(=N-Q_3)(N-Z_1-Q_1)(Q_2)$

| ex. | $Ar_1$ | $R_1$ | $Ar_2$ | $R_2$ | $NR_3R_4$ | $Z_1$ | $Q_1$ | $Q_2$ | $Q_3$ | sel (solvate) | m.p. °C. | A/B | $[\alpha]_D^{20(1)}$ |
|---|---|---|---|---|---|---|---|---|---|---|---|---|---|
| 1 | naphthyl | H | phenyl | H | piperidine | $(CH_2)_2$ | $CH_3$ | $NH$ | $NH$ | HCl, 2,5$H_2O$ | 210 | 40/60 | |
| 2 | naphthyl | H | phenyl | H | piperidine | bond | H | $-N-(CH_2)_2-N-$ | | HCl, 2,5$H_2O$ | 228 | 45/55 | |
| 3 | naphthyl | H | phenyl | H | pyrrolidine | $(CH_2)_5$ | OH | $NH$ | $NH$ | HCl, $H_2O$ | 231 | 60/40 | |
| 4 | naphthyl | H | phenyl | H | pyrrolidine | $(CH_2)_3$ | $NHCOOC(CH_3)_3$ | $NH$ | $NH$ | Base, 0,5$H_2O$ | 150 | 50/50 | |
| 5 | naphthyl | H | phenyl | H | pyrrolidine | bond | H | $-N-(CH_2)_3-N-$ | | Base, 0,5$H_2O$ | 171 | 25/75 | |
| 6 | naphthyl | H | phenyl | H | pyrrolidine | 1,4-cyclohexyl-bis(CH_2)(3) | $NH_2$ | $NH$ | $NH$ | 2HCl, 4$H_2O$, 0,5 $C_3H_2O$ | 260 | 0/100(2) | +19°2 |
| 7 | naphthyl | H | phenyl | H | pyrrolidine | 1,4-cyclohexyl-bis(CH_2)(3) | $N(CH_3)_2$ | $NH$ | $NH$ | 2HCl, 3$H_2O$ | 225 | 0/100(2) | +21°4 |

TABLE 1-continued $Ar_1-SO_2-N\underset{R_1}{}-C\underset{R_2}{\overset{}{-}}-C\underset{CH_2}{\overset{O}{-}}-N\underset{H}{\overset{}{-}}-CH-CH_2-C\underset{}{\overset{O}{=}}-N\underset{R_4}{\overset{R_3}{-}}$ with $Ar_2$ substituent and para-substituted phenyl bearing $C(=N-O_3)-N(Z_1-Q_1)(O_2)$

| ex. | Ar₁ | R₁ | Ar₂ | R₂ | NR₃R₄ | Z₁ | Q₁ | NO₂ | NO₃ | sel (solvate) | m.p. °C. | A/B | [α]_D^{20(1)} |
|---|---|---|---|---|---|---|---|---|---|---|---|---|---|
| 8 | naphthyl | H | phenyl | H | piperidine | —CH(CH₃)— | CH₃ | NH | NH | Base, H₂O | 192 | 40/50 | |
| 9 | naphthyl | H | phenyl | H | pyrrolidine | (CH₂)₂ | CH₃ | NH | NH | HCl, H₂O | 262 | 30/60 | |
| 10 | naphthyl | H | phenyl | H | pyrrolidine | (CH₂)₃ | CH₃ | NH | NH | HCl, ⅓H₂O | 270 | 50/50 | |
| 11 | naphthyl | H | phenyl | H | pyrrolidine | (CH₂)₃ | CH₃ | NCH₃ | NH | Base, 1,5H₂O | 200 | 60/40 | |
| 12 | naphthyl | H | phenyl | H | pyrrolidine | (CH₂)₃ | N(CH₃)₂ | NH | NH | 2HCl, 0,5H₂O | 172 | 50/50 | |
| 13 | naphthyl | H | tolyl(CH₂) | H | pyrrolidine | (CH₂)₃ | N(CH₃)₂ | NH | NH | HCl, 2H₂O | 184 | 50/50 | |
| 14 | naphthyl | H | phenyl | H | pyrrolidine | (CH₂)₄ | N(CH₃)₂ | NH | NH | HCl, 1,5H₂O | 265 | 50/50 | |

TABLE 1-continued $Ar_1-SO_2-N-C-C-N-CH-CH_2$ structure with $R_1, R_2, O, R_3, R_4, Ar_2$ and aromatic ring with $N-Q_3$, $N-Z_1-Q_1$, $Q_2$ substituents

| ex. | Ar₁ | R₁ | Ar₂ | R₂ | NR₃R₄ | Z₁ | Q₁ | NQ₂ | NQ₃ | sel (solvate) | m.p. °C. | A/B | $[\alpha]_D^{20(1)}$ |
|---|---|---|---|---|---|---|---|---|---|---|---|---|---|
| 15 | 1-Cl-naphthyl | H | 3,4-diCl-phenyl | H | N(CH₃)(C₂H₅) | 1,4-cyclohexyl-CH₂ | N(CH₃)₂ | NH | NH | 2HCl, 6H₂O | 260 | 50/50 | |
| 16 | 2,3-diCl-phenyl | H | 4-CH₃-phenyl | H | N(CH₃)(C₂H₅) | 1,4-cyclohexyl-CH₂ | N(CH₃)₂ | NH | NH | 2HCl, 3H₂O | 230 | 50/50 | |
| 17 | 2-naphthyl | H | phenyl | H | pyrrolidinyl | 1,4-phenyl-CH₂ | NH₂ | NH | NH | 2HCl, 4H₂O | 245 | 35/65 | |
| 18 | 2-naphthyl | H | 4-CH₃-phenyl | H | pyrrolidinyl | 1,4-cyclohexyl-CH₂ (3) | N(CH₃)₂ | NH | NH | 2HCl, 2H₂O | 222 | 50/50 | |
| 19 | 2,3-diCl-phenyl | H | 4-CH₃-phenyl | H | pyrrolidinyl | 1,4-cyclohexyl-CH₂ (3) | N(CH₃)₂ | NH | NH | 2HCl, 3.5H₂O | 244 | 50/50 | |
| 20 | 2-naphthyl | H | phenyl | H | pyrrolidinyl | 1,4-phenyl-CH₂ | N(CH₃)₂ | NH | NH | 2HCl, 3H₂O | 255 | 0/100(2) | +24°5 |

TABLE 1-continued $$Ar_1-SO_2-N\underset{R_1}{\overset{R_2}{|}}-\underset{|}{\overset{O}{C}}-\underset{|}{\overset{H}{C}}-N-\underset{|}{\overset{C=O}{CH}}-\underset{R_4}{\overset{R_3}{N}}$$
$$CH_2-Ar_2$$

with Q group: phenyl-C(=N-Q_3)-N(-Q_2)-Z_1-Q_1

| ex. | Ar₁ | R₁ | Ar₂ | R₂ | NR₃R₄ | Z₁ | Q₁ | NQ₂ | NQ₃ | sel (solvate) | m.p. °C. | A/B | $[\alpha]_D^{20(1)}$ |
|---|---|---|---|---|---|---|---|---|---|---|---|---|---|
| 21 | naphthyl | H | phenyl | H | pyrrolidinyl | (CH₂)₃ | -N=CH- (imidazole) | NH | NH | 2CF₃COOH, 2H₂O | 190 | 35/65 | |
| 22 | naphthyl | H | phenyl | H | pyrrolidinyl | (CH₂)₂ | imidazole-NH | NH | NH | 2HCl, 2H₂O | 220 | 65/35 | |
| 23 | naphthyl | H | phenyl | H | pyrrolidinyl | (CH₂)₃ | imidazole-NH | NH | NH | 2HCl, 2H₂O | 242 | 50/50 | |
| 24 | naphthyl | H | phenyl | H | pyrrolidinyl | (CH₂)₅ | imidazole-NH | NH | NH | 3HCl, 3H₂O | 240 | 50/50 | |
| 25 | naphthyl | CH₃ | phenyl | H | pyrrolidinyl | (CH₂)₃ | 4-methylpyridyl | NH | NH | 2HCl, 4H₂O | 274 | 80/20 | |
| 26 | naphthyl | CH₃ | phenyl | H | pyrrolidinyl | (CH₂)₃ | N-methylpiperazinyl | NH | NH | 2HCl, 2H₂O C₃H₇OH | 245 | 40/60 | |
| 27 | naphthyl | H | phenyl | H | pyrrolidinyl | (CH₂)₂ | 3-methylphenyl | NH | NH | Base, H₂O | 150 | 15/85 | |

TABLE 1-continued $$Ar_1-SO_2-N(R_1)(R_2)-C(=O)-N(H)-CH(CH_2Ar_2)-C(=O)-N(R_3)(R_4)$$

with Q group: $-C(=N-Q_3)(N(Q_2)-Z_1-Q_1)$ on phenyl-CH$_2$

| ex. | Ar$_1$ | R$_1$ | Ar$_2$ | R$_2$ | NR$_3$R$_4$ | Z$_1$ | Q$_1$ | NQ$_2$ | NQ$_3$ | sel (solvate) | m.p. °C. | A/B | $[\alpha]_D^{20(1)}$ |
|---|---|---|---|---|---|---|---|---|---|---|---|---|---|
| 28 | naphthyl | H | phenyl | H | pyrrolidinyl | (CH$_2$)$_3$ | —COOC$_2$H$_5$ | NH | NH | HCl, H$_2$O | 228 | 50/50 | |
| 29 | naphthyl | H | phenyl | H | pyrrolidinyl | (CH$_2$)$_5$ | —CONH$_2$ | NH | NH | HCl, 2H$_2$O | 256 | 65/35 | |
| 30 | naphthyl | H | phenyl | H | pyrrolidinyl | (CH$_2$)$_6$ | —OH | NH | NH | HCl, 4H$_2$O | 160 | 75/25 | |
| 31 | naphthyl | H | o-CH$_3$-phenyl | H | pyrrolidinyl | 1,4-cyclohexylene-CH$_2$ (3) | N(CH$_3$)$_2$ | NH | NH | 2HCl, 4H$_2$O | 275 | 50/50 | |
| 32 | naphthyl | H | phenyl | H | pyrrolidinyl | (CH$_2$)$_4$ | NHCOOC(CH$_3$)$_3$ | NH | NH | Base | 165 | 50/50 | |
| 33 | naphthyl | H | phenyl | H | pyrrolidinyl | (CH$_2$)$_5$ | NHCOOC(CH$_3$)$_3$ | NH | NH | Base, 0,5H$_2$O | 180 | 55/45 | |
| 34 | naphthyl | H | phenyl | H | pyrrolidinyl | 1,3-cyclohexylene-bis-CH$_2$ | NHCOOC(CH$_3$)$_3$ | NH | NH | HCl, 2H$_2$O | 200 | 40/60 | |

TABLE 1-continued

Structure:
$Ar_1-SO_2-N(R_1)-C(R_2)-C(=O)-N(H)-CH(CH_2-Ar_2)-C(=O)-N(R_3)(R_4)$ with substituent $-Z_1-N(Q_2)-C(=N-Q_3)-Q_1$ on phenyl

| ex. | $Ar_1$ | $R_1$ | $Ar_2$ | $R_2$ | $NR_3R_4$ | $Z_1$ | $Q_1$ | $NQ_2$ | $NQ_3$ | sel (solvate) | m.p. °C. | A/B | $[\alpha]_D^{20(1)}$ |
|---|---|---|---|---|---|---|---|---|---|---|---|---|---|
| 35 | naphthyl | H | phenyl | H | pyrrolidine | $(CH_2)_6$ | $NHCOOC(CH_3)_3$ | NH | NH | HCl, $H_2O$ | 204 | 50/50 | |
| 36 | naphthyl | H | phenyl | H | pyrrolidine | $(CH_2)_7$ | $NHCOOC(CH_3)_3$ | NH | NH | HCl, $H_2O$ | 205 | 50/50 | |
| 37 | naphthyl | H | phenyl | H | pyrrolidine | $(CH_2)_8$ | $NHCOOC(CH_3)_3$ | NH | NH | HCl, $1,5H_2O$ | 215 | 50/50 | |
| 38 | naphthyl | H | phenyl | H | pyrrolidine | $(CH_2)_4$ | $NH_2$ | NH | NH | 2HCl, $1,5H_2O$ | 230 | 50/50 | |
| 39 | naphthyl | H | phenyl | H | pyrrolidine | $(CH_2)_5$ | $NH_2$ | NH | NH | 2HCl, $2,5H_2O$ | 274 | 50/50 | |
| 40 | naphthyl | H | phenyl | H | pyrrolidine | $(CH_2)_6$ | $NH_2$ | NH | NH | Base, $2/3H_2O$ | 170 | 50/50 | |
| 41 | naphthyl | H | phenyl | H | pyrrolidine | $(CH_2)_7$ | $NH_2$ | NH | NH | 2HCl, $4H_2O$ | 192 | 55/45 | |

TABLE 1-continued

| ex. | Ar$_1$ | R$_1$ | Ar$_2$ | R$_2$ | NR$_3$R$_4$ | Z$_1$ | Q$_1$ | NQ$_2$ | NQ$_3$ | sel (solvate) | m.p. °C. | A/B | $[\alpha]_D^{20(1)}$ |
|---|---|---|---|---|---|---|---|---|---|---|---|---|---|
| 42 | naphthyl | H | phenyl | H | pyrrolidine | (CH$_2$)$_8$ | NH$_2$ | NH | NH | 2HCl, 2H$_2$O | 228 | 60/40 | |
| 43 | naphthyl | H | phenyl | H | pyrrolidine | (CH$_2$)$_9$ | NH$_2$ | NH | NH | 2CF$_3$COOH, 2 H$_2$O | 238 | 50/50 | |
| 44 | naphthyl | H | 4-CH$_3$-phenyl | H | pyrrolidine | (CH$_2$)$_6$ | NH$_2$ | NH | NH | 2HCl, 2H$_2$O | 215 | 50/50 | |
| 45 | naphthyl | H | phenyl | H | pyrrolidine | (CH$_2$)$_7$ | NH$_2$ | NH | NH | 2HCl, 2,5 H$_2$O, 0,5C$_3$H$_7$OH | 245 | 0/100(2) | +38°6 |
| 46 | naphthyl | H | phenyl | H | pyrrolidine | (CH$_2$)$_4$ | -NH-C(=NH)-NH$_2$ | NH | NH | 2HCl, 2H$_2$O | 185 | 50/50 | |
| 47 | naphthyl | H | phenyl | H | pyrrolidine | 1,4-cyclohexyl-bis(CH$_2$) | NH$_2$ | NH | NH | 2(COOH)$_2$ 0,75H$_2$O | 207 | 0/100(2) | +26°6 |
| 48 | naphthyl | H | phenyl | H | pyrrolidine | 1,4-phenyl-bis(CH$_2$) | NH$_2$ | NH | NH | 2HCl, 2,5H$_2$O | 275 | 0/100(2) | +23° |

TABLE 1-continued

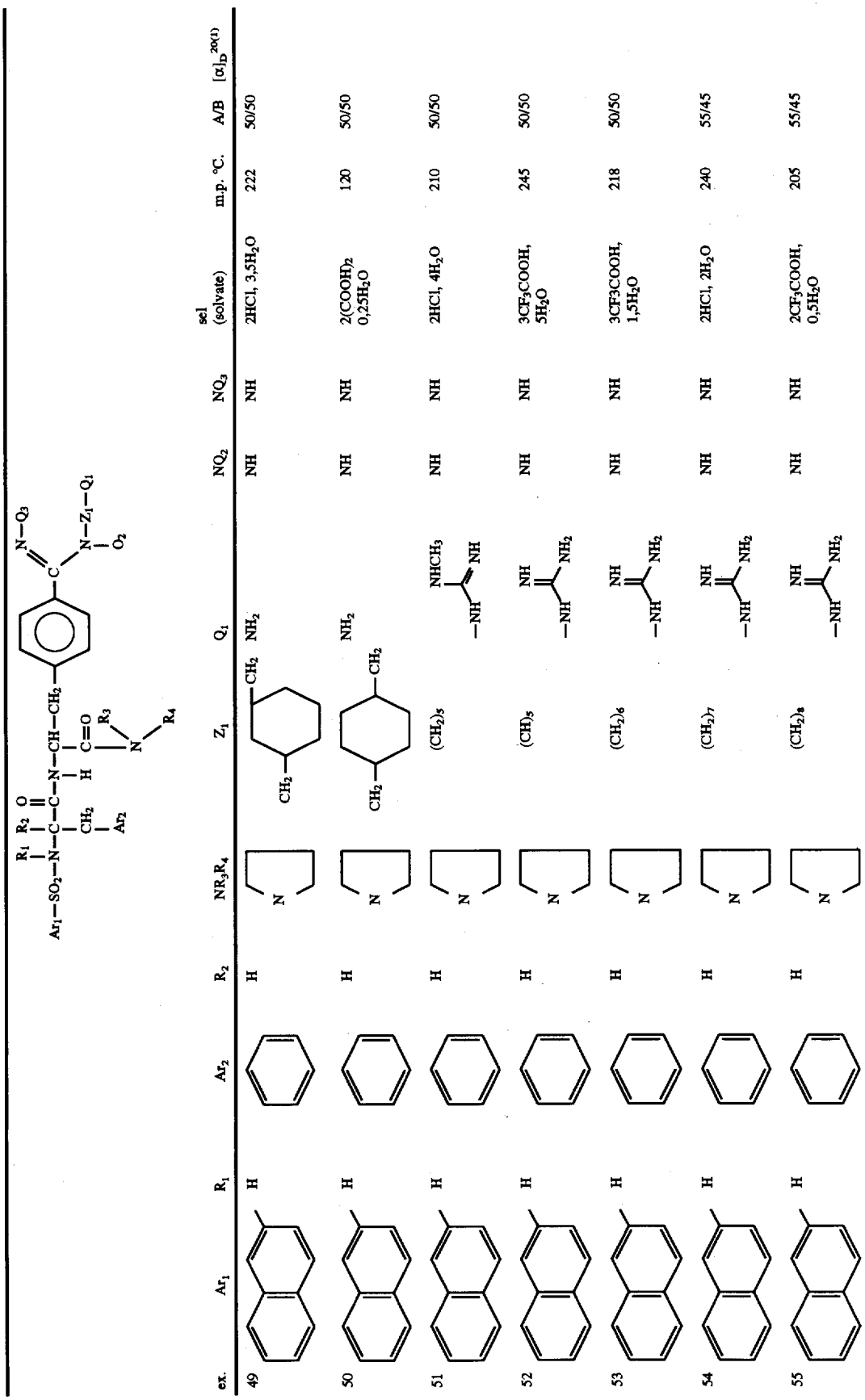

| ex. | Ar$_1$ | R$_1$ | Ar$_2$ | R$_2$ | NR$_3$R$_4$ | Z$_1$ | Q$_1$ | NQ$_2$ | NQ$_3$ | sel (solvate) | m.p. °C. | A/B | $[\alpha]_D^{20(1)}$ |
|---|---|---|---|---|---|---|---|---|---|---|---|---|---|
| 49 | naphthyl | H | phenyl | H | pyrrolidinyl | cyclohexyl-1,3-bis(CH$_2$) | NH$_2$ | NH | NH | 2HCl, 3,5H$_2$O | 222 | 50/50 | |
| 50 | naphthyl | H | phenyl | H | pyrrolidinyl | cyclohexyl-1,4-bis(CH$_2$) | NH$_2$ | NH | NH | 2(COOH)$_2$ 0,25H$_2$O | 120 | 50/50 | |
| 51 | naphthyl | H | phenyl | H | pyrrolidinyl | (CH$_2$)$_5$ | –NH–C(NHCH$_3$)=NH | NH | NH | 2HCl, 4H$_2$O | 210 | 50/50 | |
| 52 | naphthyl | H | phenyl | H | pyrrolidinyl | (CH$_2$)$_5$ | –NH–C(NH$_2$)=NH | NH | NH | 3CF$_3$COOH, 5H$_2$O | 245 | 50/50 | |
| 53 | naphthyl | H | phenyl | H | pyrrolidinyl | (CH$_2$)$_6$ | –NH–C(NH$_2$)=NH | NH | NH | 3CF$_3$COOH, 1,5H$_2$O | 218 | 50/50 | |
| 54 | naphthyl | H | phenyl | H | pyrrolidinyl | (CH$_2$)$_7$ | –NH–C(NH$_2$)=NH | NH | NH | 2HCl, 2H$_2$O | 240 | 55/45 | |
| 55 | naphthyl | H | phenyl | H | pyrrolidinyl | (CH$_2$)$_8$ | –NH–C(NH$_2$)=NH | NH | NH | 2CF$_3$COOH, 0,5H$_2$O | 205 | 55/45 | |

TABLE 1-continued

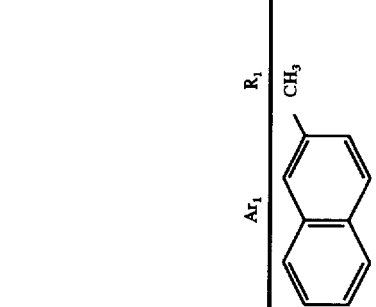

| ex. | Ar₁ | R₁ | Ar₂ | R₂ | NR₃R₄ | Z₁ | Q₁ | NQ₂ | NQ₃ | sel (solvate) | m.p. °C. | A/B | $[\alpha]_D^{20(1)}$ |
|---|---|---|---|---|---|---|---|---|---|---|---|---|---|
| 56 | naphthyl | CH₃ | phenyl | H | pyrrolidinyl | (CH₂)₃ | NCH₃—(CH₂)₃NH₂ | NH | NH | 3HCl, 5H₂O | 246 | 70/30 | |
| 57 | quinolinyl | H | 4-methyl-2-methoxyphenyl | H | pyrrolidinyl | 1,4-cyclohexylene-CH₂ (3) | N(CH₃)₂ | NH | NH | 3HCl, 4H₂O | 260 | 50/50 | |
| 58 | naphthyl | H | 4-methyl-2-methoxyphenyl | H | pyrrolidinyl | 1,4-cyclohexylene-CH₂ (3) | N(CH₃)₂ | NH | NH | 2HCl, 3H₂O | 245 | 0/100⁽²⁾ | +16°1 |
| 59 | naphthyl | H | phenyl | H | pyrrolidinyl | (CH₂)₂ | indol-2-yl NH | NH | NH | HCl | 228 | 50/50 | |
| 60 | naphthyl | H | phenyl | H | pyrrolidinyl | 1,4-cyclohexylene-CH₂ (3) | N(CH₃)₂ | NH | NH | 2HCl, 3H₂O | 220 | 100⁽⁴⁾/0 | −19°7 |
| 61 | naphthyl | H | phenyl | H | pyrrolidinyl | 1,4-cyclohexylene-CH₂ (5) | NH₂ | NH | NH | 2HCl, 2,5 H₂O | 222 | 0/100⁽²⁾ | +26° |
| 62 | naphthyl | H | 2,4-dimethylphenyl | H | N(CH₃)₂ | 1,4-cyclohexylene-CH₂ | N(CH₃)₂ | NH | NH | | 208 | | |

TABLE 1-continued $$Ar_1-SO_2-N(R_1)-C(R_2)(H)-C(=O)-N(H)-CH(CH_2Ar_2)-C(=O)-N(R_3)(R_4)$$

with Q group: 4-substituted phenyl bearing $C(=N-Q_3)(N(Z_1-Q_1)(Q_2))$

| ex. | Ar₁ | R₁ | Ar₂ | R₂ | NR₃R₄ | Z₁ | Q₁ | Q₂ | Q₃ | sel (solvate) | m.p. °C. | A/B | $[\alpha]_D^{20(1)}$ |
|---|---|---|---|---|---|---|---|---|---|---|---|---|---|
| 63 | 1-naphthyl | H | phenyl | H | pyrrolidinyl | 1,4-cyclohexyl-CH₂ (3) | N(CH₃)₂ | NH | NH | 3HCl, 3H₂O | 185 | 100(4)/0 | +50°9 |
| 64 | 2-methyl-naphthyl | H | 4-OH-phenyl | H | azepanyl | decalinyl-CH₂ (3) | N(CH₃)₂ | NH | NH | 2CF₃COOH, 3H₂O | 186 | 50/50 | |
| 65 | 4-methyl-phenyl | H | 4-Cl-phenyl | H | pyrrolidinyl | 1,4-cyclohexyl-CH₂ (3) | N(CH₃)₂ | NH | NH | 2H₂O | | 40/60 | |
| 66 | 1-naphthyl | H | phenyl | CH₃ | pyrrolidinyl | decalinyl-CH₂ (3) | N(CH₃)₂ | NH | NH | 3HCl, 3H₂O | | 60/40 | |
| 67 | quinolinyl | H | thienyl | H | pyrrolyl | decalinyl-CH₂ (5) | N(CH₃)₂ | NH | NH | 2HCl, 4H₂O | | 0/100(2) | +52° |
| 68 | 1-naphthyl | H | | H | pyrrolyl | 1,4-cyclohexyl-CH₂ (3) | N(CH₃)₂ | NH | NH | 2HCl, 3H₂O | | 50/50 | |

(1) c = 1, CH₃OH
(2) only one enantiomer in B
(3) cyclohexyl in the trans configuration
(4) only one enantiomer in A
(5) cyclohexyl in the cis configuration

We claim:

1. A compound of formula I

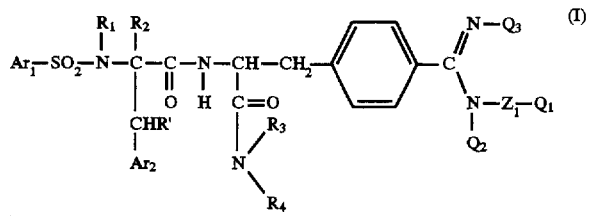

in which

- $Ar_1$ is selected from the group consisting of naphthyl and phenyl, optionally substituted by a radical selected from the group consisting of Cl, F, $(C_1-C_4)$alkyl, $(C_1-C_4)$alkoxy, hrdroxyl, and $(C_1-C_4)$dialkylamino;
- $Ar_2$ is thienyl optionally substituted by Cl, F, $(C_1-C_4)$ alkyl, $(C_1-C_4)$alkoxy or hydroxyl;
- $R_1$, $R_2$ and $R'_2$ are selected independently of each other from the group consisting of H and $(C_1-C_4)$alkyl or $R_1$ represents a bond and N is covalently bonded to $Ar_2$, or $R_2$ and $R'_2$ form a double bond, or $R_1$ or $R_2$ is covalently bonded to $Ar_2$ and represents a $(C_1-C_3)$ alkylene;
- $R_3$ and $R_4$ form, with the nitrogen atom to which they are attached, pyrrolidine;
- $Z_1$ represents $(C_1-C_{12})$alkylene, optionally interrupted by a radical selected from the group consisting of $(C_5-C_7)$ cycloalkyl and phenyl or substituted with a radical selected from the group consisting of $(C_5-C_7)$ cycloalkyl and phenyl;
- $Q_1$ is selected from the group consisting of methyl, amino, $(C_1-C_4)$alkoxycarbonylamino, $(C_1-C_4)$alkylamino, di$(C_1-C_4)$-alkylamino, pyrrolidinyl, piperidino, morpholino, piperazinyl, 4-$(C_1-C_4)$alkylpiperazinyl, amidino, $(C_1-C_4)$-alkylamidino, guanidino, $(C_1-C_4)$ alkylguanidino, pyridyl, imidazolyl, pyrimidinyl, indolyl, hydroxy, $(C_1-C_4)$alkoxy, $(C_2-C_8)$ alkoxycarbonyl, N-[amino$(C_1-C_4)$alkyl]-N-[$(C_1-C_4)$ alkyl]amino, carbamoyl, phenyl and phenyl substituted by a radical selected from the group consisting of Cl, F, $(C_1-C_4)$alkyl, $(C_1-C_4)$alkoxy and hydroxyl;
- $Q_2$ is selected from the group consisting of H and $(C_1-C_4)$ alkyl;
- $Q_3$ is selected from the group consisting of H and $(C_1-C_4)$ alkyl or $Q_1$ and $Q_3$ are attached to form a heterocycle and together represent $(C_2-C_3)$alkylene, whereas $Z_1$ represents a bond, in the form of pure enantiomer or mixture thereof in any proportions as well as its salt with acid.

2. A compound according to claim 1 of formula I, in which $Z_1$ represents $(C_4-C_9)$alkylene and $Q_1$ contains a nitrogen atom attached to $Z_1$.

3. A compound according to claim 1, in which $Q_1$ represents an amino, guanidino, amidino, $(C_1-C_4)$alkoxycarbonylamino, $(C_1-C_4)$alkylamino, di$(C_1-C_4)$alkylamino, guanidino, $(C_1-C_4)$alkylguanidino, or N-[amino$(C_1-C_4)$ alkyl]-N-]$(C_1-C_4)$]alkylamino group.

4. A pharmaceutical composition comprising a therapeutically active amount of a compound of formula I according to claim 1, in the form of pure enantiomers or a mixture of enantiomers or one of their pharmaceutically acceptable salts combined with at least one excipient.

5. A compound of formula I

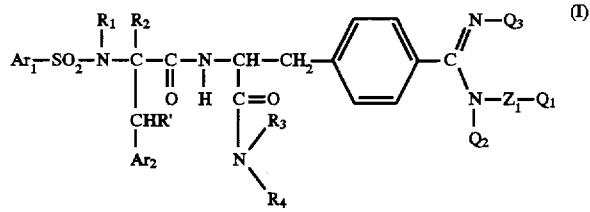

in which

- $Ar_1$ is selected from the group consisting of naphthyl and phenyl, optionally substituted by a radical selected from the group consisting of Cl, F, $(C_1-C_4)$alkyl, $(C_1-C_4)$alkoxy, hydroxyl and $(C_1-C_4)$dialkylamino;
- $Ar_2$ is phenyl optionally substituted by Cl, F, $(C_1-C_4)$ alkyl, $(C_1-C_4)$alkoxy or hydroxyl;
- $R_1$, $R_2$ and $R'_2$ are selected independently of each other from the group consisting of H and $(C_1-C_4)$alkyl or $R_1$ represents a bond and N is covalently bonded to $Ar_2$, or $R_2$ and $R'_2$ may form a double bond, or $R_1$ or $R_2$ is covalently bonded to $Ar_2$ and represents a $(C_1-C_3)$ alkylene;
- $R_3$ and $R_4$ form, with the nitrogen atom to which they are attached, pyrrolidine;
- $Z_1$ represents $(C_1-C_{12})$alkylene, optionally interrupted by a radical selected from the group consisting of $(C_5-C_7)$ cycloalkyl and phenyl or substituted with a radical selected from the group consisting of $(C_5-C_7)$ cycloalkyl and phenyl;
- $Q_1$ is selected from the group consisting of pyrrolidinyl, piperidino, morpholino, piperazinyl, 4-$(C_1-C_4)$ alkylpiperazinyl, pyridyl, imidazolyl, pyrimidinyl and indolyl,
- $Q_2$ is selected from the group consisting of H and $(C_1-C_4)$ alkyl;
- $Q_3$ is selected from the group consisting of H and $(C_1-C_4)$ alkyl or $Q_1$ and $Q_3$ are attached to form a heterocycle and together represent $(C_2-C_3)$alkylene, whereas $Z_1$ represents a bond, in the form of pure enantiomer or mixture thereof in any proportions as well as its salt with acid.

6. A compound according to claim 5 of formula I, in which $Z_1$ represents $(C_4-C_9)$alkylene and $Q_1$ contains a nitrogen atom attached to $Z_1$.

7. A pharmaceutical composition comprising a therapeutically active amount of a compound of formula I according to claim 5, in the form of pure enantiomers or a mixture of enantiomers or one of their pharmaceutically acceptable salts combined with at least one excipient.

* * * * *